United States Patent [19]

Hofen et al.

[11] 4,070,253

[45] Jan. 24, 1978

[54] PROCESS FOR SEPARATING SOLUTIONS CONTAINING PROPYLENE OXIDE

[75] Inventors: Willi Hofen, Rodenbach; Rolf Wirthwein, Hanau; Karl-Hermann Reissinger, Leverkusen; Jörg Krekel, Essen, all of Germany

[73] Assignees: Bayer Aktiengesellschaft, Leverkusen; Deutsche Gold- und Silber-Scheideanstal vormals Roessler, Frankfurt am Main, both of Germany

[21] Appl. No.: 678,826

[22] Filed: Apr. 28, 1976

[30] Foreign Application Priority Data

Apr. 30, 1975 Germany .............................. 2519292

[51] Int. Cl.$^2$ ...................... B01D 3/10; C07D 301/02
[52] U.S. Cl. ................................. 203/75; 260/348.37
[58] Field of Search ..................... 203/75, 82, 74, 81, 203/69, 60; 260/348.5 L

[56] References Cited

U.S. PATENT DOCUMENTS

| | | |
|---|---|---|
| 3,151,047 | 9/1964 | Moon et al. .............................. 203/75 |
| 3,350,417 | 10/1967 | Binning et al. ......................... 203/75 |
| 3,350,418 | 10/1967 | Bowe et al. ............................. 203/75 |
| 3,350,419 | 10/1967 | Null et al. ............................... 203/75 |
| 3,654,094 | 4/1972 | Yamagishi et al. ........... 260/348.5 L |

*Primary Examiner*—Wilbur L. Bascomb, Jr.
*Attorney, Agent, or Firm*—Burgess, Dinklage & Sprung

[57] ABSTRACT

Process for separating a solution, which essentially contains propylene oxide, propylene, a carboxylic acid containing 1 to 4 carbon atoms and benzene, by distillation. The solution is fed to a first distillation stage in which propylene, propylene oxide and an amount of the benzene contained in the solution such that the top product from this first distillation contains 20 to 70% by weight of benzene are distilled off over the top at a pressure of 1.0 to 2.5 bars, and in which the carboxylic acid and the remaining benzene are obtained as the sump product. The top product from the first distillation is fed to a second distillation column in which propylene and possibly present small fractions of components which boil lower than propylene oxide are distilled off over the top and a sump product which essentially consists of propylene oxide and benzene is obtained and part of this is returned as reflux to the first distillation column.

20 Claims; 1 Drawing Figure

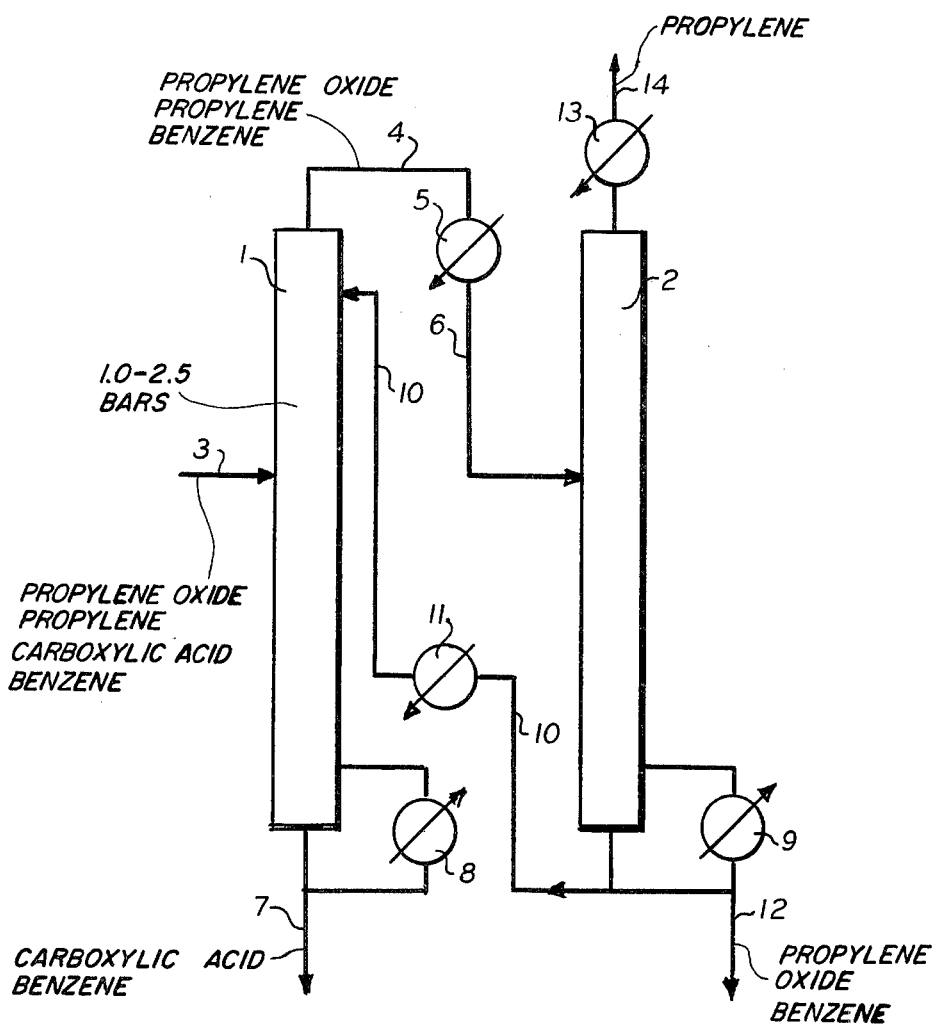

PROCESS FOR SEPARATING SOLUTIONS CONTAINING PROPYLENE OXIDE

The present invention relates to a process for separating mixtures which essentially consist of propylene oxide, a carboxylic acid, propylene and benzene.

When propylene oxide is prepared according to previously known processes, a mixture which essentially contains propylene oxide, a low-molecular carboxylic acid and propylene as well as, in some cases, propane, is generally obtained as the reaction product. Very frequently a mixture of this type is present as a solution in a solvent which has a boiling point which lies between those of propylene oxide and the carboxylic acid.

A reaction mixture which, in addition to propylene oxide, contains a low-molecular aliphatic carboxylic acid is obtained, for example, from the non-catalytic direct oxidation of propylene with molecular oxygen by the process according to DOS (German Published Specification) No. 1,543,114. With this process, mixtures of propylene oxide and carboxylic acids, such as formic acid or acetic acid, are obtained (DOS (German Published Specification) No. 1,543,174, page 8, line 18).

Other processes for the preparation of propylene oxide, in which, in addition to propylene oxide, a carboxylic acid is present in the reaction mixture, are based on the oxidation, optionally in a hydrophobic organic solvent, of propylene with a percarboxylic acid, for example peracetic acid or performic acid as selective oxidising agents for propylene. However, the carboxylic acid obtained together with the epoxide must be removed as rapidly as possible. In this context it is stated, for example, in D. Swern, Organic Peroxides, Whiley Interscience 1971, Vol. II, page 433, first complete paragraph: "Product workup is particularly important in commercial epoxidations. Complete removal of organic and inorganic acids from the epoxide is necessary to prevent subsequent epoxide cleavage or polymerization (or both), and to obtain a product acceptable for use with polyvinyl chloride". In particular, it is necessary to prevent further reaction of the propylene oxide with the aliphatic carboxylic acid, with cleavage of the ring to give the corresponding propylene glycol monoester. This reaction between propylene oxide and aliphatic carboxylic acids can already take place during the reaction or also during the separation of the reaction mixtures. The result of this is that with these previously known processes for the preparation of propylene oxide, the yield of purified propylene oxide is markedly reduced (DOS (German Published Specification) No. 2,013,877, page 3, lines 9 to 16). The attack of the carboxylic acid on the propylene oxides is thus an extremely undesirable reaction which reduces the yield. Consequently, a number of processes have been disclosed in which measures are taken in order as far as possible to prevent this reaction when working up reaction mixtures, containing propylene oxide, to separate them into the individual constituents. According to DAS (German Published Specification) No. 1,543,174, for example, the procedure is that a stream of liquid obtained after the propylene oxide reaction stage is transferred into an acid-removing distillation, where organic acids are obtained as the bottom product and propylene oxide, propylene and propane as well as other low-boiling components are distilled off as the top product. The propylene and propane are removed from this top product by distillation in a second column and crude propylene oxide is obtained as the bottom product (DAS (German Published Specification) No. 1,543,174, steps d, e and f). There are also processes in which very large amounts of carboxylic acid are present in the reaction mixture from the preparation of propylene oxide, for example in the case of processes for the preparation of propylene oxide in which aliphatic percarboxylic acids are used as the epoxidising agent. It must also be taken into account that an organic solvent, such as ethyl acetate or benzene, is frequently additionally present, when such reaction mixtures are worked up. For processes of this type it is proposed, for example according to German Pat. No. 1,802,241, to separate propylene oxide continuously from mixtures of propylene, acetic acid and possibly other constituents having a higher boiling point by first removing propylene oxide and propylene conjointly from the other constituents by distillation under an elevated pressure in the presence of an inert solvent, which has a boiling point between 50° and 100° C, and then separating propylene oxide and propylene from one another in a further distillation. Thus, in this case, propylene oxide is obtained together with propylene as a two-component mixture as the top product from an initial distillation stage (German Pat. No. 1,802,241, column 2, lines 12 to 14 and lines 57 to 59). The residual mixture, which essentially consists of the inert solvent and the acetic acid, is obtained as the sump from this distillation (German Pat. No. 1,802,241, column 2, lines 25 to 28).

According to this process, furthermore, the distillate from the first column is fed directly to the second distillation stage for the separation of propylene oxide and propylene. When propylene oxide is separated off by distillation, 4.4 to 6.2% by weight of high-boiling products, relative to the propylene oxide charged into the distillation, are formed (German Pat. No. 1,802,241, column 3, line 2 and also column 4, lines 24 to 26).

In another process, which is described in DOS (German Published Specification) No. 2,013,877, the separation and the purification of propylene oxide are carried out by introducing a mixture containing propylene oxide, propylene, acetic acid and peracetic acid, as well as a solvent, into a first pressure distillation column and there subjecting it to distillation at a pressure in the range from about 1.3 to 5.0 bars, acetic acid and the solvent being removed as the residue from the base and a distillate containing propylene and propylene oxide being obtained at the top of the column, liquefying the gaseous constituents of the distillate, thereafter transferring the liquefied constituents together with the condensed part of the distillate into a second pressure distillation column and there subjecting this mixture to distillation, propylene being distilled off through the top of the column and propylene oxide being obtained as the sump product from the distillation column. In this process according to DOS (German Published Specification) No. 2,013,877, the distillate from the first distillation, which is obtained at the top of the column and which contains a mixture of propylene and propylene oxide, is liquefied by refrigeration and/or by compression. The requisite complete condensation is thus not effected by industrial water but requires the technical effort of brine cooling or of a compression stage (DOS (German Published Specification) No. 2,013,877, page 6, lines 6 to 10 and also page 11, line 27 to page 12, first line). A further considerable disadvantage of this process is that a very high reflux ratio is employed to separate propylene and propylene oxide on the one hand from acetic acid and the solvent on the other hand. According to the data given in DOS (German Published Specification) No. 2,013,877, on page 11, line 17, the reflux ratio is 10. Thus, the mixture of propylene and propylene oxide which is to be separated off must be vapourised and condensed ten times. This is associated with a correspondingly high vapourisation and condensation. Accordingly, distinct losses of propylene oxide still arise with the process (DOS (German Published Specification) No. 2,013,877, page 8, final paragraph to page 9, line 16, and also page 13, line 9). The high reflux ratio in this distillation column thus necessitates a correspondingly high steam load in the column, which in turn entails correspondingly large dimensions of the column.

In contrast, a process for separating a solution, which essentially contains propylene oxide, propylene, a carboxylic acid containing 1–4 carbon atoms and benzene, by distillation has now been found which is characterised in that the solution is fed to a first distillation column and propylene, propylene oxide and an amount of the benzene contained in the solution such that the top product from this first distillation contains 20 to 70% by weight of benzene are distilled off over the top at a pressure of 1.0 to 2.5 bars, the carboxylic acid and the remaining benzene being obtained as the sump product, and the top product from the first distillation is fed to a second distillation column in which propylene and possibly present small fractions of components which boil lower than propylene oxide are distilled off over the top and a sump product which essentially consists of propylene oxide and benzene is obtained and part of this is returned as reflux into the first distillation column Carboxylic acids containing 1 to 4 carbon atoms which may be mentioned are aliphatic monocarboxylic acids, e.g. formic acid, acetic acid, propionic acid, isobutyric acid and n-butyric acid. Carboxylic acids which, for example, are substituted by fluorine or chlorine, such as trifluoroacetic acid, monofluoroacetic acid, monochloroacetic acid, 1-chloropropionic acid, 2-chloropropionic acid, 2-fluoropropionic acid and 1-fluoropropionic acid, can also be used.

Preferably, propylene oxide-containing mixtures which contain acetic acid, propionic acid, n-butyric acid or isobutyric acid are used for the process according to the invention. The process according to the invention is very particularly suitable for the separation of mixtures containing acetic acid or propionic acid.

The concentration of propylene oxide and of carboxylic acid in the benzene starting solution can vary within wide limits. The concentration of propylene oxide is generally 1 to 50, preferably 3 to 30,% by weight. Solutions having a propylene oxide content of 5 to 20% by weight are very particularly suitable.

The carboxylic acid content is generally 3 to 50, preferably 5 to 40,% by weight. The propylene content can be up to the solubility limit of propylene in the particular mixture to be separated. In addition, small amounts of other compounds can also be present. It is particularly advantageous to apply the process according to the invention to mixtures which are obtained from the preparation of propylene oxide by reaction of propylene with a percarboxylic acid in benzene solution. In addition to propane, which is generally contained in the starting propylene, small amounts of acetaldehyde, methyl formate, propionaldehyde, propylene glycol monoesters and propylene glycol diesters are generally present in such mixtures.

The proportion of benzene in the mixture to be separated by the process according to the invention is generally 20 to 80% by weight. In particular cases, however, the concentration can also be above or below this concentration range. Mixtures containing 30 to 70% by weight of benzene are particularly suitable for the separation according to the invention.

When the process according to the invention is carried out in the customary manner, a mixture of the described composition is metered into the first distillation column and propylene, propylene oxide and part of the benzene are distilled off over the top at a pressure of 1.0 to 2.5, preferably 1.2 to 2.0, bars. The amount of benzene which is taken over the top in the distillation is generally 20 to 70, preferably 25 to 55,% by weight of the top product. Preferentially, the distillate contains 30 to 40% by weight of benzene. The propylene oxide content of the top product of the first distillation column is in general from 25 to 70% by weight. During the distillation the temperature at the top of the distillation column is generally 35° to 70° C. A particular advantage of the process according to the invention is that it is possible to cool with water at the top of the column, a cooling water temperature of 20° to 35° C being sufficient. This means that cooling water available in large amounts as return flow from the cooling towers of industrial plants can be used.

With the distillation according to the invention, the return of the whole or part of the top product from the first distillation column as reflux into the first column is avoided. Rather, the top product from the first column, appropriate after condensation, is passed into the second distillation column. In the second distillation unit, propylene is distilled off, together with compounds which have a lower boiling point than propylene oxide and which may be present, for example propane, and propylene oxide and the fraction of benzene distilled over from the first column is obtained as the sump product. Part of the sump product from the second distillation unit is returned in the requisite amount as reflux into the first distillation unit. The remaining part of the sump product from the second distillation column is withdrawn. This sump product is a benzene solution which essentially contains propylene oxide and which can be separated in the customary manner, for example by close fractionation, into pure propylene oxide on the one hand and benzene on the other hand. The reflux ratio in the first distillation column is generally from 3 to 0.1 and frequently from 2.4 to 0.3 in the process according to the invention. Preferably it is from 2.0 to 0.4. A reflux ratio of from 1.5 to 0.5 is particularly advantageous.

The pressure in the second distillation column can be varied within wide limits and the distillation can be carried out at normal pressure, elevated pressure or at reduced pressure. Preferably, the second distillation column is operated at elevated pressure. It is particularly advantageous to operate the column at a pressure which is so high that a substantial part of the top product, which is in the form of a vapour, can be condensed with water at the top of the column. In general, the second distillation column is operated at pressures of from 3 to 40 bars. A preferred pressure range is at pressures from 4 to 15 bars. The condensation in the second distillation unit is carried out in the customary manner. For example, the propylene, mixed with any propane which may be present, obtained at the top can be condensed and the liquid top product can be returned as reflux to the column and removed from the column in the liquid form. However, it is also possible to use a dephlegmator as the condensation unit, in which case propylene leaves the distillation column in the gaseous form. The gaseous propylene can be freed from any propylene oxide which may be present in the propylene gas evolved, for example by washing with a suitable solvent. The gaseous propylene washed in this way can, however, also be liquefied, for example by compression, and the whole or part thereof can be returned as reflux into the second column. An appropriate reflux ratio in this second distillation column can readily be determined. In principle, it can be varied within wide limits. It can have values of, for example, from 5 to 15. The use of a reflux ratio which may be of this order of magnitude entails no particular expenditure on equipment for the process since at the top of this second distillation column there is essentially only propylene, mixed with any propane which may be present. The total amount of this propene/propane mixture is so small that even a high reflux ratio entails no particular expenditure.

All the customary equipment, for example packed columns or trayed columns, can be used as distillation columns for the first and the second distillation stage. All the customary types of packings and trays are suitable. Known equipment, such as circulation reboilers, thin layer evaporators or falling flow evaporators, can also be used as the reboiler.

The mixture containing propylene oxide and carboxylic acid can be fed in the liquid or gaseous form into the first distillation unit. However, it is also possible to use specific embodiments for feeding the product. Thus, for example, the liquid mixture can be passed over a vaporiser unit, for example a thin layer evaporator, and gas and liquid from this vaporisation stage can be fed separately into the column. This can be advantageous insofar as it is possible to achieve a particularly rapid separation of propylene oxide from carboxylic acid.

In a particular embodiment of the process according to the invention a distillation line consisting of 2 columns 1 and 2 is used, as can be seen from FIG. 1. A solution of 8 to 14% by weight of propylene oxide, 1 to 5% by weight of propylene and 25 to 35% by weight of propionic acid in benzene is passed into column 1 via 3. The entire propylene and propylene oxide and an amount of benzene such that the distillate from column 1 contains 30 to 35% by weight of benzene are distilled over the top at a pressure of 1.2 to 1.5 bars, a sump temperature of 95° to 110° C and a top temperature of 30° to 65° C. The distillate from column 1 obtained at 4 is condensed as far as possible in the condenser 5 using cooling water at 24° C. The condensate and fractions which are not condensed are passed via 6 into the distillation column 2. The total amount of carboxylic acid and the remainder of the benzene are withdrawn from the sump of column 1 via 7. The sump of column 1 is heated by means of reboiler 8.

The second distillation column 2 is operated at a pressure of 5 to 6 bars. A propylene-free mixture of about 30% by weight of benzene and about 70% by weight of propylene oxide is obtained as the sump of this second column, which is heated by means of reboiler 9, and part of this mixture is passed as reflux to column 1 via 10 and the cooler 11. The reflux ratio in column 1 is from 1 to 2. The other part of the propylene-free sump from columm 2 is withdrawn via 12 and is the desired carboxylic acid-free solution of propylene oxide in benzene. At the top of column 2, propylene issues from the column as a gas after cooling, downstream of cooler 13, and is removed via 14.

The particular advantage of the process according to the invention is that the formation of propylene glycol esters is so greatly reduced that the formation of these byproducts can no longer be detected by means of the customary analytical methods. A further advantage of the process according to the invention is that the condensation in the first column can be carried out using water as the coolant, a water temperature of 20–30° C being sufficient. A particular economic advantage of the process according to the invention is the loss-free separation of the propylene oxide from a low-molecular aliphatic carboxylic acid by distillation with a surprisingly small reflux ratio. Surprisingly, it has been found to be advantageous to distil off part of the benzene over the top in the first distillation column and to return the propylene-free and propane-free sump product from the second distillation column as reflux to the first column. By means of the measure, according to the invention, of taking part of the benzene over the top, with the propylene oxide, in the first column, it is possible to reduce the reflux ratio to values of between 1.5 and 0.5. Compared with the state of the art, this signifies a substantial reduction in the expenditure on evaporation and condensation and a corresponding reduction (smaller dimensions) in the first distillation column.

EXAMPLE 1

(see also FIG. 1)

716 g per hour of a reaction mixture from the reaction of propylene with a benzene solution of perpropionic acid for the preparation of propylene oxide are fed as a liquid via 3 to the distillation colum 1. The composition of the reaction mixture fed to column 1 was 12.0% by weight of propylene oxide, 25.1% by weight of propionic acid, 61.9% by weight of benzene, 1.0% by weight of propylene as well as small amounts of low-boiling and high-boiling by-products. 586 g per hour of a mixture consisting of 69.3% by weight of benzene and 30.7% by weight of propionic acid were withdrawn at the sump of distillation column 1. The top product from the column was condensed in condenser 5 and then fed via 6 to a further distillation column 2. In column 2, the propylene dissolved in the feed stream 6 was distilled off at the top via 14 in an amount of 7 g per hour. The reflux into column 2 was produced with the aid of the dephlegmator 13. 292 g per hour of propylene-free crude propylene oxide, which contains 70.0% by weight of propylene oxide and 30.0% by weight of benzene as well as traces of low-boiling impurities, are obtained as the sump of column 2. 169 g per hour of this sump product are passed as reflux, via 10 to column 1 and 123 g per hour are withdrawn via 12 for further working up. Column 1 was operated at a pressure of about 1.3 bars. Temperatures of 36° C at the top and 104° C in the sump of the column were set up. The top temperature of 36° C made it possible to use cooling water at a temperature of 24° C in the condenser 5. Column 2 was operated at a pressure of 5.3 bars, the temperatures being −3° C at the top of the column and 94° C in the sump. The condensation of the reflux in the dephlegmator 13 was carried out with a refrigerant. The reflux ratio at which column 2 was operated was 10. The sump product from column 2, in so far as it was used as reflux for column 1, was cooled to a temperature of 35° C in the cooler 11.

Losses of propylene glycol due to the formation of propylene glycol esters were not detectable.

EXAMPLE 2

(comparison experiment)

Experiments were carried out under the same conditions as in Example 1, but the procedure was such that benzene contents of between 0 and 70% by weight were obtained in the sump product of column 2. The distillation conditions and the results achieved are summarised in Table 1.

It can be seen from Table 1 that it is advantageous to work with benzene contents of 20 to 70% by weight in the sump product from column 2. With benzene concentrations below 20% by weight, that is to say with more extensive separation of the benzene in column 1, the effort required for separation (reflux ratio, efficiency of the column (number of theoretical plates)), becomes greater and this results in longer residence times and thus longer contact times between propylene oxide and propionic acid in the column, which promote the formation of propylene glycol esters and thus increase the loss of propylene oxide. However, if the amount of benzene passed over with the distillate in column 1 is too large, losses of propylene oxide again arise.

Table I

| Benzene content in crude propylene oxide (sump from column 2) (% by weight) | Propylene content in the top vapour (% by weight) | Column pressure (bars) | Temperature top of the column (° C) | Temperature sump of the column (° C) | Reflux ratio | Number of trays Rectifying section | Number of trays Stripping section | Propylene oxide losses (% of feed) |
|---|---|---|---|---|---|---|---|---|
| 0 | 2.26 | about 1.3 | 32 | 105 | 2.4 | 12 | 15 | 0.2 |
| 10.0 | 2.26 | about 1.3 | 33 | 104 | 2.1 | 4 | 15 | 0.1 |
| 20.0 | 2.33 | about 1.3 | 34 | 104 | 1.7 | 4 | 15 | 0.1 |
| 30.0 | 2.40 | about 1.3 | 36 | 104 | 1.3 | 4 | 16 | not detectable |
| 50.0 | 2.00 | about 1.3 | 41 | 106 | 1.0 | 5 | 18 | not detectable |
| 70.0 | 1.22 | about 1.3 | 52 | 110 | 1.0 | 5 | 18 | 0.1 |
| 80.0 | 0.82 | about 1.3 | 60 | 124 | 1.0 | 5 | 19 | 0.2 |
| 83.7 | 0.67 | about 1.3 | 64 | 153 | 1.0 | 5 | 19 | 0.5 |

EXAMPLE 3

Using the same experimental arrangement as described in Example 1, 685 g per hour of a reaction mixture consisting of 12.3% by weight of propylene oxide, 24.8% by weight of acetic acid, 61.9% by weight of benzene and 1.0% by weight of propylene were distilled. 558 g per hour of a mixture consisting of 68.7% by weight of benzene and 31.3% by weight of acetic acid were withdrawn as the sump product from column 1. The top product from column 1 was fed, after condensing in condenser 5, via 6 to column 2, in which 7 g per hour of propylene were obtained over the top via 14 and 290 g per hour of a mixture consisting of 70% by weight of propylene oxide and 30% by weight of benzene were obtained as the sump. The sump product from column 2 was passed, via 10, as reflux in an amount of 170 g per hour to column 1. 120 g per hour were withdrawn from the sump of column 2 via 12. The temperatures in column 1, which was operated at a pressure of 1.33 bars, were 36° C at the top and 102° C at the sump.

Again, no losses of propylene oxide were found in the overall balance over the distillation.

EXAMPLE 4

The procedure was as in Example 3 but the reaction mixtures for the preparation of propylene oxide contained, as the carboxylic acids, propionic acid, formic acid and isobutyric acid respectively in place of acetic acid. The distillation conditions and the results obtained are summarized in Table 2.

Table 2

| Carboxylic acid | Benzene content in the crude propylene oxide* (% by weight) | Column pressure (bars) | Temperature top (° C) | Temperature sump (° C) | Reflux ratio | Number of plates Rectifying section | Number of plates Stripping section | Propylene oxide losses (% of feed) |
|---|---|---|---|---|---|---|---|---|
| Formic acid | 30 | about 1.3 | 36 | 100 | 1.3 | 3 | 21 | not detectable |
| Acetic acid | 30 | about 1.3 | 36 | 102 | 1.3 | 3 | 18 | not detectable |
| Propionic acid | 30 | about 1.3 | 36 | 103 | 1.3 | 2 | 16 | not detectable |
| Isobutyric acid | 30 | about 1.3 | 36 | 103 | 1.3 | 2 | 15 | not detectable |

*in the sump product from column (2)

EXAMPLE 5

(Comparison Example)

The procedure was as in Example 1 but part of the product stream flowing out of condenser 5 via 6, and not the sump product from column 2, was used as reflux for column 1.

850 g per hour of a reaction mixture consisting of 11.8% by weight of propylene oxide, 24.6% by weight of propionic acid, 62.4% by weight of benzene and 1.2% by weight of propylene as well as small fractions of low-boiling and high-boiling impurities were fed as a liquid to distillation column via 3. 697 g per hour of a mixture consisting of 69.9% by weight of benzene and 30.1% by weight of propionic acid were withdrawn from the sump of column 1 via 7. The top product from the column was condensed in condenser 5 and the liquid outflow was divided into 200 g per hour reflux going to column 1 and 153 g per hour take-off going to column 2. The composition of the outflow from condenser 5 was 68.6% by weight of propylene oxide, 21.9% by weight of benzene and 9.5% by weight of propylene as well as traces of low-boiling impurities. In column 2, the feed product was freed from propylene in the same manner as described in Example 1. The propylene was withdrawn in an amount of 10 g per hour at the top of column 2 via 14. 143 g per hour of crude propylene oxide, the composition of which was 70% by weight of propylene oxide and 30% by weight of benzene, were withdrawn from the sump of column 2 via 12. Column 1 was again operated at a pressure of 1.33 bars. The temperatures were 104° C in the sump and 19° C at the top of the column. A refrigerant had to be used as the coolant at the top of the column.

We claim:

1. Process for separating a solution comprising propylene oxide, propylene, carboxylic acid containing 1-4 carbon atoms and benzene, by distillation, comprising distilling the solution in a first distillation stage to provide an overhead product rich in propylene and propylene oxide and containing 20-70% by weight of benzene and a bottoms product rich in carboxylic acid and containing the remaining benzene, at a pressure of 1.0-2.5 bars, and distilling said overhead product in a second distillation stage to provide an overhead product comprising propylene and a bottoms product comprising benzene rich in propylene oxide and recycling part of the bottoms of the second distillation stage to the first distillation as reflux for the first distillation stage.

2. Process of claim 1, wherein the overhead product of the first distillation stage is 25 to 70% by weight of propylene oxide.

3. Process of claim 1, wherein the pressure of the first distillation stage is 1.2-2.0 bars, and the pressure of the second distillation stage is 4-15 bars.

4. Process of claim 1, wherein the overhead product of the first distillation stage contains 25-55% by weight of benzene.

5. Process of claim 1, wherein the overhead product of the first distillation stage contains 30-40% by weight of benzene.

6. Process of 2, wherein the pressure of the first distillation stage is 1.2-2.0 bars, and the pressure of the second distillation stage is 4-15 bars.

7. Process of claim 6, wherein the overhead product of the first distillation stage contains 25-55% by weight of benzene.

8. Process of claim 6, wherein the overhead product of the first distillation stage contains 30-40% by weight of benzene.

9. Process of claim 1, wherein the carboxylic acid is acetic acid.

10. Process of claim 1, wherein the carboxylic acid is propionic acid.

11. Process of claim 1, wherein said solution is 1-50% by weight propylene oxide, 3-50% by weight of carboxylic acid, 20-80% by weight of benzene, and the amount of propylene is up to the solubility thereof in the solution.

12. Process of claim 1, wherein the top temperature of the first distillation stage is 35°-70° C.

13. Process of claim 12, wherein the overhead product of the first distillation stage is cooled with water to provide cooled overhead product and said cooled product is introduced into the second distillation stage so that none of the cooled overhead product of the first distillation stage is employed as reflux.

14. Process of claim 12, wherein the pressure of the second distillation stage is 3-40 bars.

15. Process of claim 6, wherein said solution is 1-50% by weight propylene oxide, 3-50% by weight of carboxylic acid, 20-80% by weight of benzene, and the amount of propylene is up to the solubility thereof in the solution, and the top temperature of the first distillation stage is 35°-70° C. and the overhead product of the first distillation stage is cooled with water to provide cooled overhead product and said cooled overhead product is introduced into the second distillation stage so that none of the cooled overhead product of the first distillation stage is employed as reflux.

16. Process of claim 1, wherein the bottoms product of the second distillation stage contains the fraction of benzene distilled over from the first distillation stage.

17. Process of claim 1, wherein the overhead product of the first distillation stage is cooled with water for condensation of overhead product, the temperature of the cooling water being 20°-35° C.

18. Process of claim 1, wherein the refulx ratio for the first distillation stage, obtained by said recycling of bottoms product of the second distillation stage to the first distillation stage, is 3 to 0.1.

19. Process of claim 1, wherein the bottoms product of the second distillation stage contains the fraction of benzene distilled over from the first distillation stage, the overhead product of the first distillation stage is cooled with water for condensation of overhead product, the temperature of the cooling water being 20°-35° C, and the reflux ratio for the first distillation stage, obtained by said recycling of bottoms product of the second distillation stage to the first distillation stage, is 3 to 0.1.

20. Process of claim 13, wherein the bottoms product of the second distillation stage contains the fraction of benzene distilled over from the first distillation stage, the overhead product of the first distillation stage is cooled with water for condensation of overhead product, the temperature of the cooling water being 20°-35° C, and the reflux ratio for the first distillation stage, obtained by said recycling of bottoms product of the second distillation stage to the first distillation stage, is 3 to 0.1.

* * * * *